(12) United States Patent
Gilmore et al.

(10) Patent No.: US 6,742,392 B2
(45) Date of Patent: Jun. 1, 2004

(54) METHOD AND APPARATUS FOR INDUCING ULTRASONIC WAVES INTO RAILROAD RAILS

(75) Inventors: Robert Snee Gilmore, Charlton, NY (US); John Erik Hershey, Ballston Lake, NY (US); David Michael Davenport, Niskayuna, NY (US); Daniel White Sexton, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 10 days.

(21) Appl. No.: 10/283,424

(22) Filed: Oct. 29, 2002

(65) Prior Publication Data

US 2004/0079157 A1 Apr. 29, 2004

(51) Int. Cl.[7] .................................................. G01N 29/04
(52) U.S. Cl. ...................................................... 73/643
(58) Field of Search .......................... 73/643, 636, 602, 73/578

(56) References Cited

U.S. PATENT DOCUMENTS

| | | | |
|---|---|---|---|
| 3,786,672 A | * 1/1974 | Gaerttner | 73/643 |
| 4,004,455 A | 1/1977 | McKee et al. | |
| 4,164,873 A | * 8/1979 | Bottcher et al. | 73/643 |
| 4,468,966 A | 9/1984 | Bradshaw | |
| 4,662,224 A | 5/1987 | Turbe | |
| 4,777,824 A | * 10/1988 | Alers et al. | 73/643 |
| 4,932,618 A | 6/1990 | Davenport et al. | |
| 5,386,727 A | 2/1995 | Searle | |
| 5,721,379 A | * 2/1998 | Palmer et al. | 73/643 |
| 5,903,517 A | 5/1999 | Futsuhara et al. | |
| 5,907,294 A | 5/1999 | Welte et al. | |
| 6,031,790 A | 2/2000 | Futsuhara et al. | |
| 6,262,573 B1 | 7/2001 | Wojnarowski et al. | |
| 6,292,432 B1 | 9/2001 | Futsuhara et al. | |
| 6,324,912 B1 | 12/2001 | Wooh | |
| 6,424,150 B2 | 7/2002 | Kwun et al. | |
| 2001/0019263 A1 | * 9/2001 | Kwun et al. | 324/217 |
| 2001/0033049 A1 | * 10/2001 | Gurule | 269/53 |

FOREIGN PATENT DOCUMENTS

GB 2371623 A * 7/2002 .......... G01N/29/26

* cited by examiner

*Primary Examiner*—Hezron Williams
*Assistant Examiner*—Rose M. Miller
(74) *Attorney, Agent, or Firm*—Robert B. Reesner, III; Armstrong Teasdale LLP (57) ABSTRACT

A method and apparatus for nondestructive testing a railroad rail is provided. The method includes locating at least one magnetic exciter adjacent to the rail, the at least one magnetic exciter includes an emitting end and a longitudinal axis extending perpendicularly through the emitting end, discharging the energy storage circuit through the at least one magnetic exciter such that only a magnetic pulse enters the rail at a location of the exciter, and controlling a shape of the magnetic pulse. The apparatus includes at least one magnetic exciter adjacent to a rail, a energy storage circuit electrically coupled to the at least one magnetic exciter the energy storage circuit is configured to supply a shaped current pulse to the at least one exciter, and a power source electrically coupled to the energy storage circuit.

23 Claims, 5 Drawing Sheets

METHOD AND APPARATUS FOR INDUCING ULTRASONIC WAVES INTO RAILROAD RAILS

BACKGROUND OF THE INVENTION

This invention relates generally to railroad rails and more particularly to methods and apparatus for inducing ultrasonic waves into railroad rails.

Some known rail inspection techniques include eddy current analysis wherein perturbations in an electric current induced into the rail is indicative of defects, and electromagnetic analysis, wherein perturbations in magnetic flux induced into the rail are examined to reveal anomalies. Eddy current analysis and electromagnetic analysis have range limitations that make their use more time consuming and more expensive than using ultrasonic analysis. To facilitate inspection, other known inspection techniques include ultrasonic analysis wherein reflections of sound waves induced into the rail are evaluated to locate and characterize defects. Some known ultrasonic techniques use a piezoelectric principle to induce ultrasonic waves into railroad rails. A piezoelectric transducer is held in close contact with the rail while activated to induce ultrasonic waves into the rail. The piezoelectric technique has disadvantages that limits its usefulness as a cost-effective and reliable inspection tool. For example, the piezoelectric transducer generates transverse waves which have a limited range in the rail.

BRIEF DESCRIPTION OF THE INVENTION

In one aspect, a method of inducing ultrasonic waves into a railroad rail is described. The method includes locating at least one magnetic exciter adjacent to the rail, the at least one magnetic exciter includes an emitting end and a longitudinal axis extending perpendicularly through the emitting end, discharging the energy storage circuit through the at least one magnetic exciter such that only a magnetic pulse enters the rail at a location of the exciter, and controlling a shape of the magnetic pulse.

In another aspect of the present invention, an apparatus for inducing ultrasonic waves into a railroad rail is described. The apparatus includes at least one magnetic exciter adjacent to the rail, an energy storage circuit electrically coupled to the at least one magnetic exciter, the energy storage circuit configured to supply a shaped current pulse to the at least one exciter, and a power source electrically coupled to the energy storage circuit configured to charge the energy storage circuit with electrical energy.

In a further aspect, a railroad locomotive is described. The locomotive includes a platform having a first end and a second end, a propulsion system coupled to the platform for supporting and propelling the platform on a pair of rails, and a rail ultrasonic wave inducement system comprising at least one magnetic exciter, a energy storage circuit electrically coupled to the at least one magnetic exciter, and a power source electrically coupled to the energy storage circuit, the at least one magnetic exciter is coupled to the locomotive such that the at least one magnetic exciter moves in concert with the locomotive and maintains a position adjacent to a rail, the energy storage circuit is configured to supply at least one of sequential current pulses to the at least one magnetic exciter and simultaneous current pulses to the at least one magnetic exciter according to a predetermined configuration, the energy storage circuit is further configured to control a shape of the pulses.

In yet another aspect, a railroad vehicle is described. The vehicle includes a platform having a first end and a second end, a truck coupled to the platform for supporting the platform on a pair of rails, and a rail ultrasonic wave inducement system comprising at least one magnetic exciter, a energy storage circuit electrically coupled to the at least one magnetic exciter, and a power source electrically coupled to the energy storage circuit, the at least one magnetic exciter is coupled to the vehicle such that the at least one magnetic exciter moves in concert with the vehicle and maintains a position adjacent to a rail, the energy storage circuit is configured to supply at least one of sequential current pulses to the at least one magnetic exciter and simultaneous current pulses to the at least one magnetic exciter according to a predetermined configuration, the energy storage circuit is further configured to control a shape of the pulses.

DETAILED DESCRIPTION OF THE INVENTION

Figure 1:
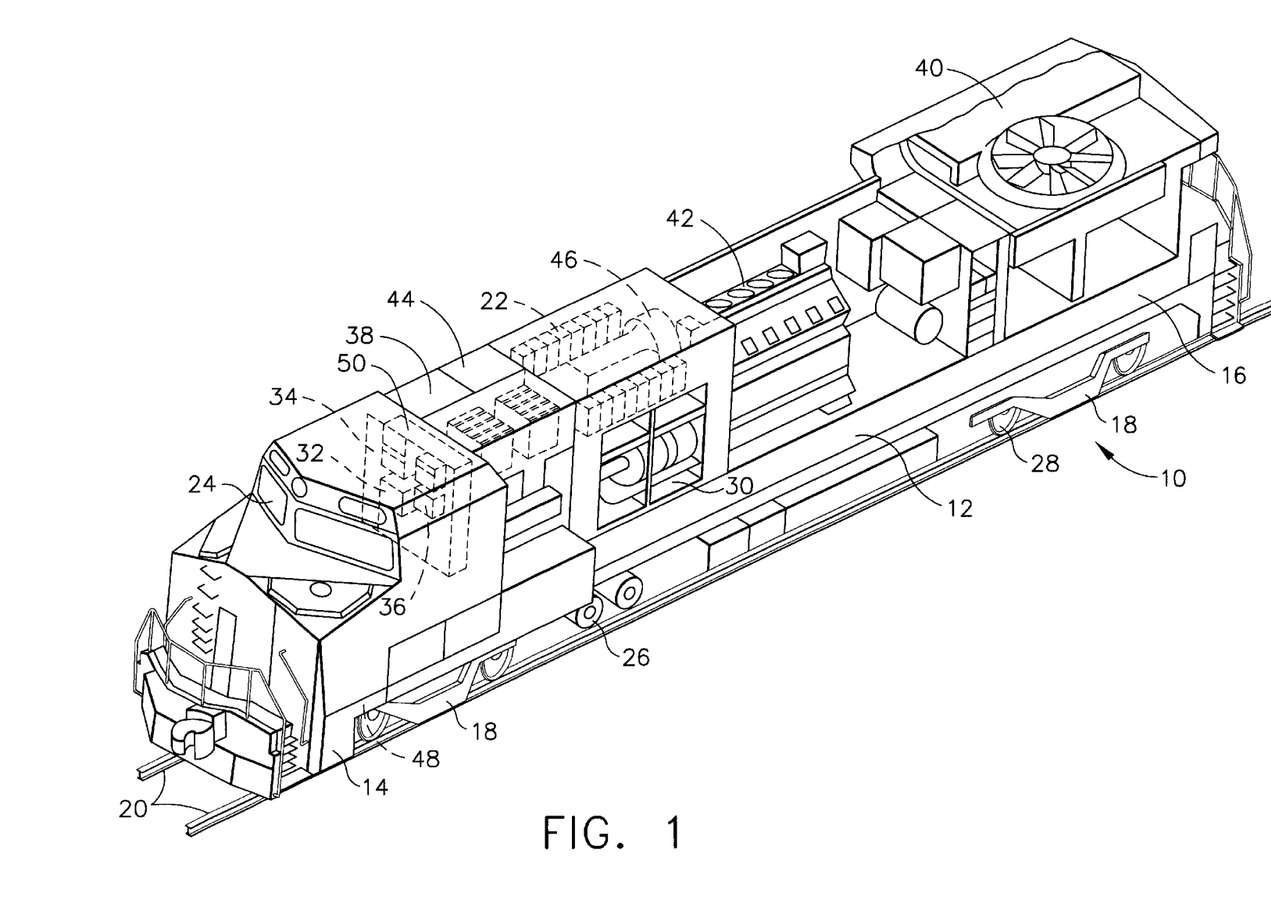
FIG. 1 is a partial cut away view illustrating an exemplary locomotive

FIG. 1 is a partial cut away view of an exemplary locomotive 10. Locomotive 10 includes a platform 12 having a first end 14 and a second end 16. A propulsion system 18, or truck is coupled to platform 12 for supporting, and propelling platform 12 on a pair of rails 20. An equipment compartment 22 and an operator cab 24 are coupled to platform 12. An air and air brake system 26 provides compressed air to locomotive 10, which uses the compressed air to actuate a plurality of air brakes 28 on locomotive 10 and railcars (not shown) behind it. An auxiliary alternator system 30 supplies power to all auxiliary equipment. An intra-consist communications system 32 collects, distributes, and displays consist data across all locomotives in a consist.

A cab signal system 34 links the wayside (not shown) to a train control system 36. In particular, system 34 receives coded signals from a pair of rails 20 through track receivers (not shown) located on the front and rear of the locomotive. The information received is used to inform the locomotive operator of the speed limit and operating mode. A distributed power control system 38 enables remote control capability of multiple locomotive consists coupled in the train. System 38 also provides for control of tractive power in motoring and braking, as well as air brake control.

An engine cooling system 40 enables engine 42 and other components to reject heat to cooling water. In addition, system 40 facilitates minimizing engine thermal cycling by maintaining an optimal engine temperature throughout the load range, and facilitates preventing overheating in tunnels. An equipment ventilation system 44 provides cooling to locomotive 10 equipment.

A traction alternator system 46 converts mechanical power to electrical power which is then provided to propulsion system 18. Propulsion system 18 enables locomotive 10 to move and includes at least one traction motor 48 and dynamic braking capability. In particular, propulsion system 18 receives power from traction alternator 46, and through traction motors 48 moves locomotive 10. Locomotive 10 systems are monitored by an on-board monitor (OBM) system 50. OBM system 50 keeps track of incidents occurring in the systems with an incident log.

Figure 2:
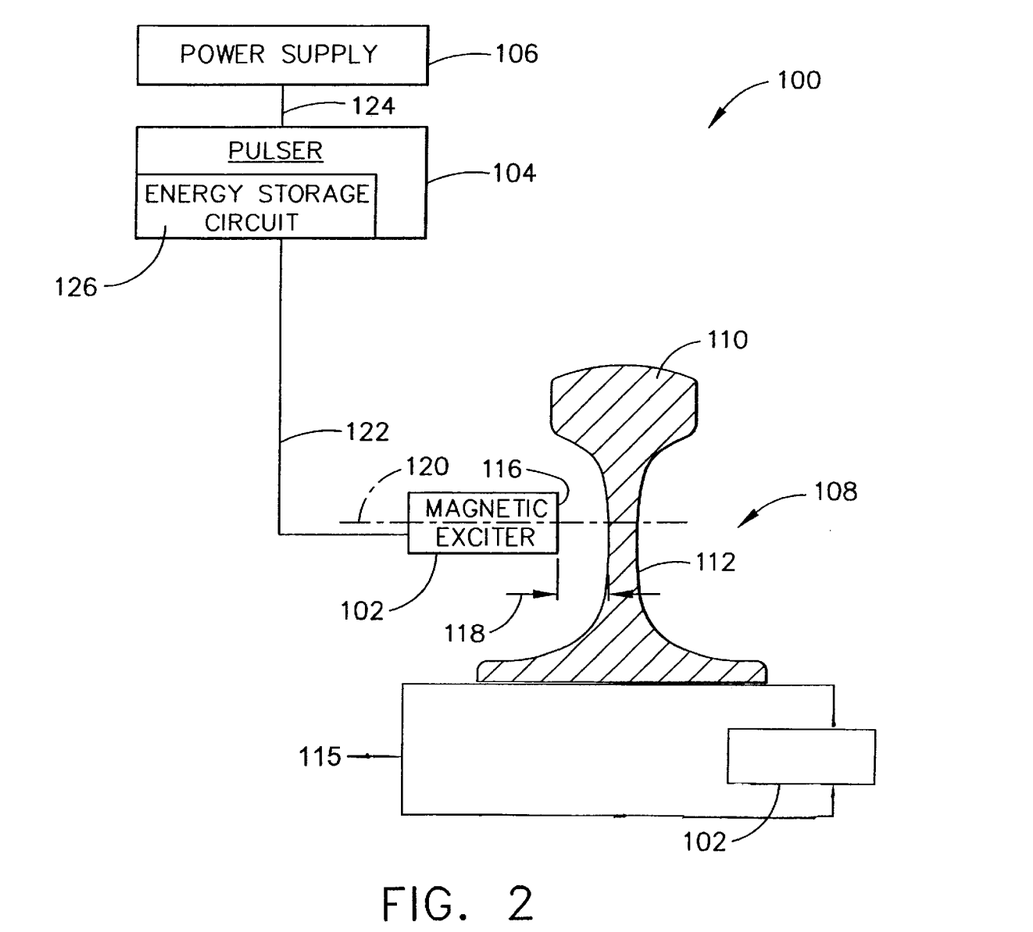
FIG. 2 is a sectional view of a railroad rail and an ultrasonic wave inducement system.

FIG. 2 is a cross-sectional view of a railroad rail and an ultrasonic wave inducement system 100. System 100 includes a magnetic exciter 102, a pulser 104, and a power supply 106. A rail 108 includes a rail head 110, a rail web 112, and a rail base 114. Base 114 is a longitudinally extending member, a first edge of web 112 is coupled to base 114 such that web 112 extends perpendicularly therefrom. Rail head 110 is coupled to a second edge of web 112. Magnetic exciter 102 is coupled to locomotive 10 such that exciter 102 is fixed in a position. More specifically, as locomotive 10 moves along rail 108, a first face 116 of exciter 102 is maintained at a substantially fixed distance 118 from rail 108, for example a distance 118 less than a diameter of first face 116. Additionally, exciter 102 is positioned such that a longitudinal axis 120 of exciter 102 is substantially perpendicular to a rail longitudinal axis 121. For example, longitudinal axis 120 is substantially perpendicular to longitudinal axis 121 when the angular difference between longitudinal axis 120 and longitudinal axis 121 is within the range of about 70 degrees to about 110 degrees. In an alternative embodiment, exciter 102 is coupled to a vehicle, such as a rail car or rail road service vehicle, that is not a locomotive.

Exciter 102 is electrically coupled to pulser 104 by cable 122. In an exemplary embodiment, pulser 104 is electrically coupled to power supply 106 through cable 124. In an alternative embodiment, pulser 104 and power supply 106 are included in a single equipment enclosure wherein pulser 104 and power supply 106 are electrically coupled via wiring internal to the enclosure. Power supply 106 is configured to supply alternating current (AC) electrical power to pulser 104. In an alternative embodiment, power supply 106 supplies at least one voltage of direct current (DC) power to pulser 104. Power supply 106 is supplied with electrical power from a convenient power source supplied from locomotive 10 or an auxiliary source independent from locomotive 10.

In the exemplary embodiment, exciter 102 includes a magnetic core (not shown) that is magnetically coupled to a winding (not shown). The core is oriented such that magnetic lines of flux exit face 116 substantially parallel to face 116, for example, at an angle of less than or equal to about twenty degrees. In an alternative embodiment, the core is oriented in exciter 102 such that magnetic lines of flux exit magnetic lines of flux substantially perpendicular to face 116, for example when an angular difference between the magnetic lines of flux and face 116 is within the range of about 70 degrees to about 110 degrees.

Pulser 104 includes an energy storage circuit 126 including a capacitive reactance for storing electrical energy for supplying exciter 102, and electronic devices for shaping an output pulse supplied to exciter 102. In the exemplary embodiment, pulser 104 also includes a computer configured to precisely control an output pulse of pulser 104.

In an alternative embodiment, exciter 102 is buried adjacent rail base 114. In yet another embodiment exciter 102 may be located inside a hollow rail tie 115 adjacent to rail base 114. Pulser 104 and power supply 106 are each buried proximate exciter 102, or in a suitable enclosure nearby. In one embodiment, exciter 102 is stationary with respect to rail 108 and may be located in a cofferdam for easy maintenance access. Pulser 104 may be remotely controlled via a wireless communications device or via a track-signaling device.

Figure 3:
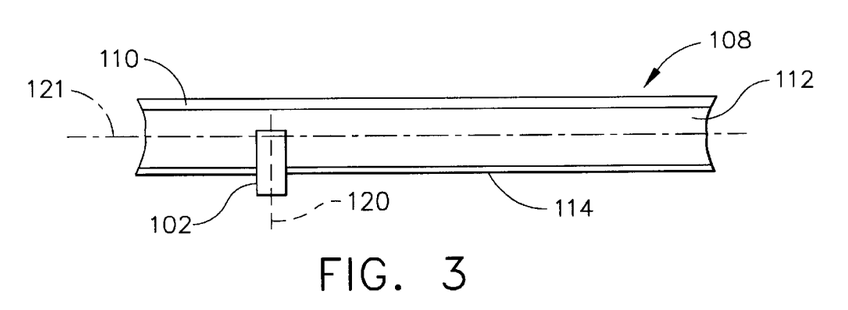
FIG. 3 is a side elevational view of a rail illustrating an exemplary position of a magnetic exciter that may be used with the ultrasonic wave inducement system shown in FIG. 2.
Figure 4:
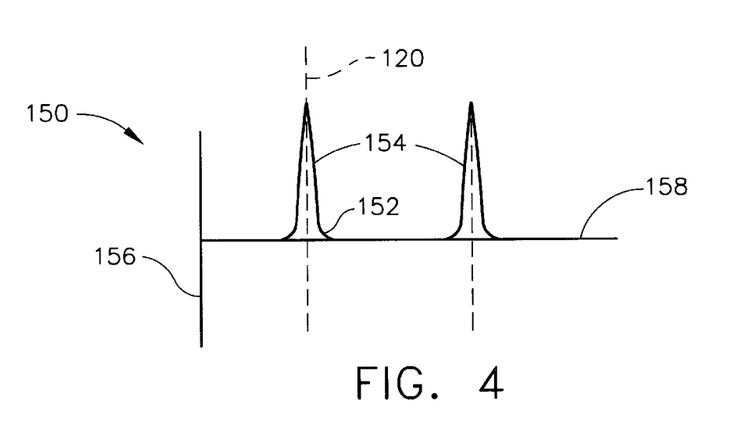
FIG. 4 is a graph illustrating exemplary ultrasonic pulses that may be obtained with the ultrasonic wave inducement system shown in FIG. 2.

FIG. 3 is a side elevational view of rail 108 illustrating an exemplary position of a magnetic exciter 102. FIG. 4 is a graph 150 illustrating exemplary trace 152 of a plurality of ultrasonic pulses 154 induced into rail 108 by exciter 102. Vertical axis 156 represents an amplitude of pulses 154 and horizontal axis 158 represents a time in which pulses 154 are traveling through rail 108 at a constant velocity with respect to each other. Longitudinal axis 120 is illustrated as the point of origin of the pulses 154 shown in FIG. 4.

In operation, distance 118 is predetermined based on physical interference objects associated with rail 108, such as bolting hardware, grounding fixtures, and switching devices and also on magnetic coupling considerations. As distance 118 between rail 108 and exciter 102 is reduced, a magnetic coupling between rail 108 and exciter 102 is facilitated to be improved.

Power supply 106 supplies charging power to energy storage circuit 126 internal to pulser 104. Pulser 104 discharges energy storage circuit 126 such that a series of current waveforms of a pre-determined shape and a pre-determined frequency are generated and supplied to exciter 102 through cable 122. The waveforms supplied to exciter 102 generate a magnetic field pulse at face 116, which penetrates rail 108. An interaction between the magnetic field and rail 108 generates an ultrasonic pulse 154 inside rail 108 where axis 120 passes through rail 108.

After pulse 154 is induced into rail 108, pulse 154 travels away from axis 120 at a velocity influenced by several factors including, but not limited to, the material composition of rail 108, the temperature of rail 108, and the amount of stress induced into rail 108. As pulse 154 moves away from axis 120, exciter 102 induces a subsequent pulse into rail 108. The frequency of pulses 154 is determined by a time constant that is controlled by pulser 104. As pulses 154 move away from axis 120 the amplitudes of pulses 154 are attenuated and their usefulness for evaluating rail 108 is diminished because pulses 154 become indistinguishable from electrical noise in detecting circuitry and ultrasonic noise in rail 108 from sources other than exciter 102. To facilitate increasing the distance that pulses 154 travel from axis 120 before attenuating below a useful amplitude, the amplitude of pulse 154 is increased at the time it is induced into rail 108.

Figure 5:
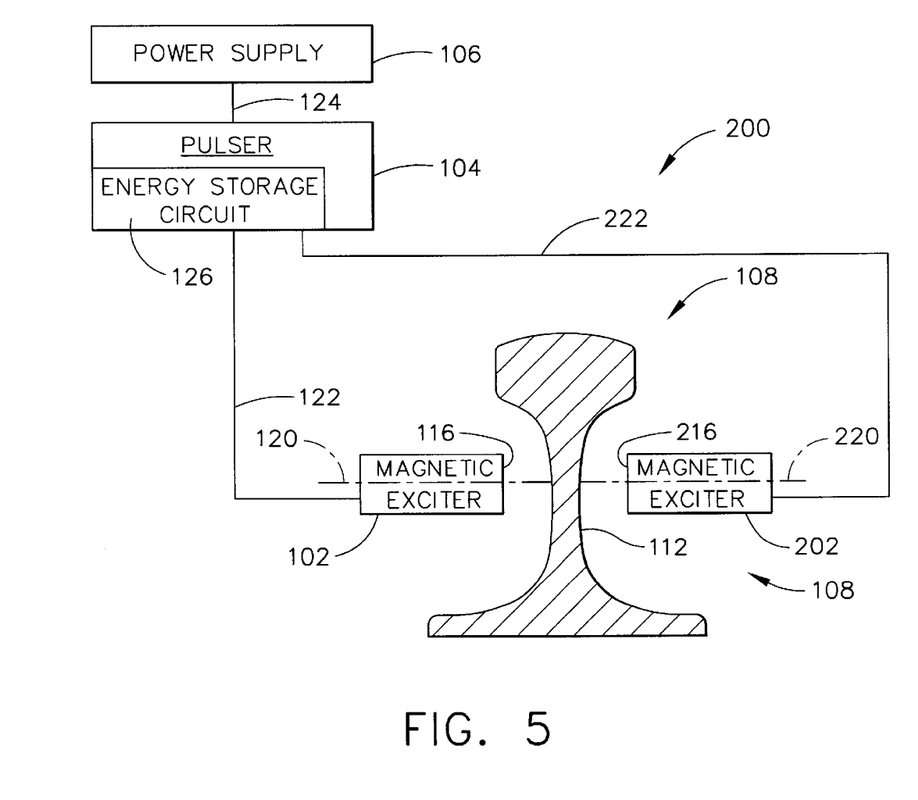
FIG. 5 is a sectional view of a railroad rail including an alternative embodiment an ultrasonic wave inducement system.

FIG. 5 is a sectional view of a railroad rail including an alternative embodiment of an ultrasonic wave inducement system 200. Components of system 200 that are identical to components of system 100 are identified in FIG. 5 using the same reference numerals used in FIG. 2. Accordingly, ultrasonic wave inducement system 200 includes rail 108, magnetic exciter 102, pulser 104, power supply 106, and interconnecting cables 122 and 124. Ultrasonic wave inducement system 200 also includes a second magnetic exciter 202 including a face 216 and a longitudinal axis 220, and a cable 222 that electrically couples exciter 202 to pulser 104.

Exciter 202 is positioned such that longitudinal axis 220 of exciter 202 is substantially coplanar with longitudinal axis 120, for example, a vertical angular difference between axis 220 and axis 120 at least one of less than about twenty degrees and equal to twenty degrees, and both axes 220 and 120 are substantially parallel to the ground at substantially the same height above the ground. For example, a difference in height above the ground between axes 120 and 220 of less than about four inches. Longitudinal axis 220 and longitudinal axis 121 intersect at a node 224. Longitudinal axis 120 and longitudinal axis 121 intersect at a node 226. A lateral distance 230, is the distance between nodes 224 and 226. In the exemplary embodiment, distance 230 is set at zero or an integral multiple of the wavelength of a pulse 254 and a pulse 256. In an alternative embodiment, distance 230 is set to a distance that facilitates physical installation of exciters 102 and 202 and pulser 104 controls a timing of pulses 254 and 256. In the exemplary embodiment, exciter 202 is identical to exciter 102. In an alternative embodiment, exciters 102 and 202 are configured differently to account for different physical interference objects that can be unique to one side of rail 108. Pulser 104 supplies shaped current pulses to exciters 102 and 202 substantially simultaneously, for example within about twenty microseconds. In a separate mode of operation pulser 104 supplies shaped current pulses to exciters 102 and 202 sequentially. In an alternative embodiment, pulser 104 supplies shaped current pulses to exciters 102 and 202 alternately simultaneously and sequentially.

Figure 6:
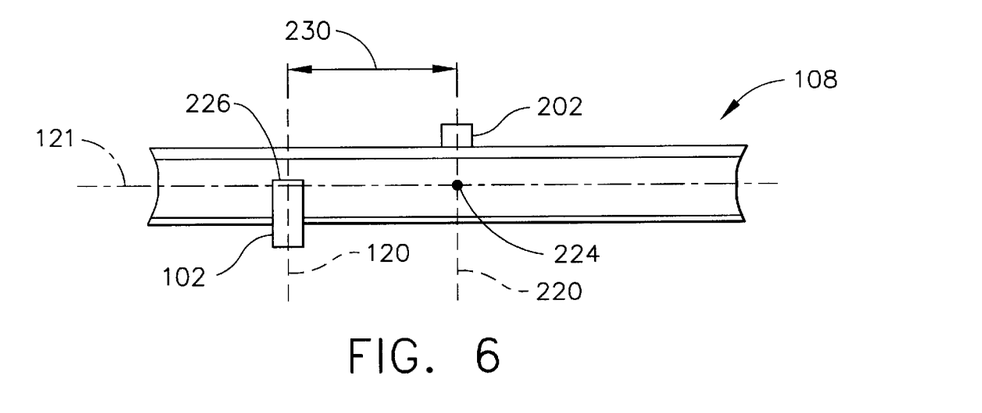
FIG. 6 is a side elevational view of a rail illustrating an alternative position of a pair of magnetic exciters that may be used with the ultrasonic wave inducement system shown in FIG. 2.
Figure 7:
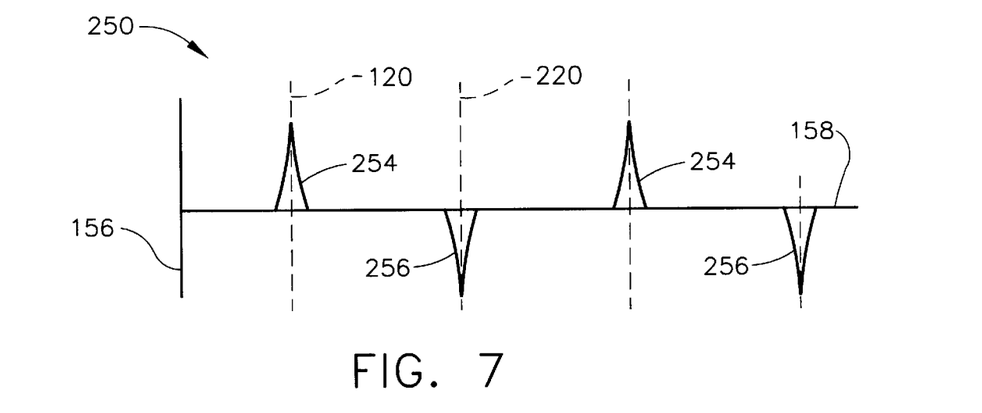
FIG. 7 is a graph of exemplary ultrasonic pulses that may be obtained with the ultrasonic wave inducement system shown in FIG. 5.

FIG. 6 is a side elevational view of rail 108 illustrating an alternative position of a pair of magnetic exciters 102 and 202 that may be used with the ultrasonic wave inducement system shown in FIG. 5. FIG. 7 is a graph 250 of exemplary ultrasonic pulses 254 and 256 that may be obtained with the ultrasonic wave inducement system shown in FIG. 5. Vertical axis 156 represents an amplitude of pulses 254 and 256. Horizontal axis 158 represents a time, which because pulses 254 and 256 are traveling through rail 108 at a constant velocity with respect to each other, axis 158 also represents a wavelength. Longitudinal axis 120 and 220 are illustrated as the point of origin of the pulses 254 and 256, respectively shown in FIG. 4.

In operation, exciters 102 and 202 are coupled to a locomotive or railcar and move in concert with the locomotive or railcar, while their respective faces 116 and 216 are maintained a distance (not shown) away from rail 108. The distance between rail 108 and face 116 may be different from the distance between rail 108 and face 216 due to interference objects adjacent to rail 108.

Power supply 106 supplies charging power to energy storage circuit 126 internal to pulser 104. Pulser 104 discharges energy storage circuit 126 such that a series of current waveforms of a pre-determined shape and a pre-determined frequency are generated and supplied to exciters 102 and 202 through cables 122 and 224. The waveforms supplied to exciters 102 and 202 generate a magnetic field pulse at faces 116 and 216, respectively, which penetrates rail 108. An interaction between the magnetic fields and rail 108 generates an ultrasonic pulse 254 in rail 108 at axis 120 and an ultrasonic pulse 256 in rail 108 at axis 220. In the exemplary embodiment, pulses 254 are opposite in polarity to pulses 256 due to their respective positions on opposites sides of rail 108. In an alternate embodiment, exciter 202 is located on the same side of rail 108 as exciter 102 and pulser 104 is configured to facilitate reversing the magnetic field emitted from exciter 202 such that pulse 256 is still oriented oppositely from pulser 254.

Pulses 254 and 256 are shaped by a predetermined output of pulser 104, which is configured to discharge a plurality of shaped current pulses to exciters 102 and 202 simultaneously, sequentially and alternating between simultaneously and sequentially. Using exciter 202 in addition to exciter 102 effectively doubles the distance capability of system 200. After pulses 254 and 256 are induced into rail 108, they travel away from axis 120 and axis 220, respectively at a velocity determined by several factors including a material composition of rail 108, a temperature of rail 108, and a stress being experienced by rail 108. As pulse 254 moves away from axis 120, exciter 102 induces a subsequent pulse into rail 108, likewise, as pulse 256 moves away from axis 220, exciter 202 induces a subsequent pulse into rail 108. The frequency of pulses 254 and 256 are determined by a time constant controlled by pulser 104. As pulses 254 and 256 move away from axis 120 and 220, respectively, the amplitudes of pulses 254 and 256 are attenuated and their usefulness for evaluating rail 108 is diminished because pulses 254 and 256 become indistinguishable from electrical noise in detecting circuitry and ultrasonic noise in rail 108 from sources other than exciter 102. Because pulse 254 is of opposite polarity from pulse 256, a peak-to-peak difference in amplitude between pulse 254 and 256 is larger than either peak-to-neutral amplitude. In one embodiment, the peak-to-peak difference in amplitude between pulse 254 and 256 is twice the peak-to-neutral amplitude of pulse 254. Creating a pair of pulses with opposite polarity is an alternative method of increasing the distance the pulses travel before attenuating below a useful amplitude. In an alternative embodiment exciter 102 and 202 may be located in a fixed position adjacent to rail 108.

The above-described ultrasonic wave inducement systems and methods are cost-effective and highly reliable. Each system includes an exciter that induces an ultrasonic pulse into a railroad rail, a pulser that controls the exciters, and a power supply that provides the system with electrical energy. Such systems permit a long range testing technique to find rail flaws, cracks, and anomalies before they become severe problems. Thus, the ultrasonic wave inducement system facilitates testing of railroad rails in a cost-effective and reliable manner.

Exemplary embodiments of ultrasonic wave inducement systems are described above in detail. The systems are not limited to the specific embodiments described herein, but rather, components of each system may be utilized independently and separately from other components described herein. Each ultrasonic wave inducement system component can also be used in combination with other ultrasonic wave inducement system components.

While the invention has been described in terms of various specific embodiments, those skilled in the art will recognize that the invention can be practiced with modification within the spirit and scope of the claims.

What is claimed is:

1. A method of inducing ultrasonic waves into a railroad rail including a rail web, a first edge of the rail web coupled longitudinally to a rail base and a second opposing edge of the rail web coupled longitudinally to a rail head, the rail web includes a first side extending from the rail base to the rail head, and a second side opposite the first side, said method comprising:

locating at least one magnetic exciter adjacent to the rail, the at least one magnetic exciter including an emitting face and a longitudinal axis extending perpendicularly through the emitting face;

discharging an energy storage circuit through the at least one magnetic exciter such that only a magnetic pulse enters the rail at a location of the exciter; and controlling the magnetic pulse shape to induce ultrasonic waves into a railroad rail.

2. A method in accordance with claim 1 wherein locating at least one magnetic exciter further comprises locating the at least one magnetic exciter such that the emitting face is adjacent to the rail and the magnetic exciter longitudinal axis is perpendicular to the rail.

3. A method in accordance with claim 1 wherein locating at least one magnetic exciter comprises operationally coupling the at least one magnetic exciter to at least one of a railroad service vehicle, a railroad locomotive and a railroad train car such that the at least one magnetic exciter is configured to move with the railroad service vehicle, the railroad locomotive a or the railroad train car while remaining adjacent to the rail.

4. A method in accordance with claim 1 wherein locating at least one magnetic exciter comprises locating at least one magnetic exciter adjacent to at least one of the rail base and the rail head such that the emitting face is adjacent to the rail base or the rail head, and the exciter longitudinal axis is perpendicular to the rail.

5. A method in accordance with claim 1 wherein a first node is defined by an intersection of a longitudinal axis of a first magnetic exciter and a longitudinal axis of the rail, a second node is defined by an intersection of a longitudinal axis of a second magnetic exciter and a longitudinal axis of the rail, such that a distance $d_1$ is a distance between the first node and the second node, wherein locating at least one magnetic exciter comprises locating a first magnetic exciter adjacent to the first side of the rail and locating a second magnetic exciter adjacent to the second opposing side of the rail, the first magnetic exciter and the second magnetic exciter spaced apart a distance $d_1$.

6. A method in accordance with claim 5 wherein locating at least one magnetic exciter comprises locating a first magnetic exciter and a second magnetic exciter such that $d_1$ is equal to at least one of about zero and about an integral multiple of a predetermined wavelength of ultrasonic energy induced into the rail by the first magnetic exciter and the second magnetic exciter.

7. A method in accordance with claim 1 wherein charging an energy storage circuit further comprises charging a capacitive reactance circuit.

8. A method in accordance with claim 1 wherein discharging the energy storage circuit further comprises:

supplying a current to the at least one magnetic exciter;

generating a magnetic field from the current;

penetrating the rail with the magnetic field; and generating an ultrasonic wave in the rail using the magnetic field.

9. A method in accordance with claim 8 wherein supplying a current to the at least one magnetic exciter further comprises supplying a current pulse to the at least one magnetic exciter.

10. A method in accordance with claim 8 wherein penetrating the rail with the magnetic field further comprises:

penetrating the rail with the magnetic field such that the strength of the magnetic field is greater than the magnetic saturation point of the rail; and wherein generating the ultrasonic wave in the rail comprises generating a shaped acoustic pulse in the rail.

11. A method in accordance with claim 8 wherein generating a an ultrasonic wave in the rail further comprises generating a longitudinal wave in the rail.

12. A method in accordance with claim 1 wherein discharging the energy storage circuit further comprises:

discharging the energy storage circuit through a first magnetic exciter at a predetermined frequency; and discharging the energy storage circuit through a second magnetic exciter laterally positioned a predetermined distance $d_1$ from the first magnetic exciter such that a wave in the rail generated by the second magnetic exciter is superimposed upon a wave generated by the first magnetic exciter passing the second magnetic exciter.

13. A method in accordance with claim 1 wherein discharging the energy storage circuit further comprises:

discharging the energy storage circuit through the at least one magnetic exciter at a first predetermined frequency;

varying at least one of a capacitance, a resistance, an inductance, and a switching circuit of the energy storage circuit; and discharging the energy storage circuit through the at least one magnetic exciter at a second predetermined frequency different from the first predetermined frequency.

14. A method in accordance with claim 1 wherein locating at least one magnetic exciter adjacent to the rail further comprises locating the at least one magnetic exciter at least partially within a rail tie.

15. An apparatus for inducing ultrasonic waves into a railroad rail, said apparatus comprising:

at least one magnetic exciter adjacent to said rail;

an energy storage circuit electrically coupled to said at least one magnetic exciter, said energy storage circuit configured to supply a shaped current pulse to said at least one magnetic exciter to induce ultrasonic waves into said railroad rail; and a power source electrically coupled to said energy storage circuit and configured to charge the energy storage circuit with electrical energy.

16. An apparatus in accordance with claim 15 wherein said at least one magnetic exciter comprises:

an emitting face comprising a planar face;

a magnetic core adjacent said emitting end; and a winding surrounding at least a portion of said magnetic core.

17. An apparatus in accordance with claim 16 wherein said core is configured to facilitate emitting a magnetic field perpendicular to said planar face of said emitting end.

18. An apparatus in accordance with claim 15 wherein said energy storage circuit is configured to supply simultaneous pulses to a plurality of exciters spaced laterally a distance $d_1$ apart, wherein a first node is defined by an intersection of a longitudinal axis of a first magnetic exciter and a longitudinal axis of the rail, a second node is defined by an intersection of a longitudinal axis of a second magnetic exciter and a longitudinal axis of the rail, such that distance $d_1$ is a lateral distance between the first node and the second node, the pulses being timed to superimpose a longitudinal wave upon an existing longitudinal wave in the rail.

19. An apparatus in accordance with claim 18 wherein said energy storage circuit is configured to supply sequential pulses to the plurality of exciters.

20. An apparatus in accordance with claim 15 wherein said energy storage circuit is configured to supply a current pulse to said at least one exciter such that the magnetic field generated by said at least one magnetic exciter exceeds the saturation flux density of the rail.

21. An apparatus in accordance with claim 15 wherein said energy storage circuit is configured to control a current pulse shape supplied to said at least one magnetic exciter.

22. A railroad locomotive comprising:

a platform having a first end and a second end;

a propulsion system coupled to said platform for supporting and propelling said platform on a pair of rails; and a rail ultrasonic wave inducement system comprising at least one magnetic exciter, a energy storage circuit electrically coupled to said at least one magnetic exciter, and a power source electrically coupled to said energy storage circuit, said at least one magnetic exciter coupled to said locomotive such that said at least one magnetic exciter is movable in concert with said locomotive and maintains a position adjacent to a rail, said energy storage circuit configured to supply at least one of sequential current pulses to said at least one magnetic exciter and simultaneous current pulses to said at least one magnetic exciter according to a predetermined configuration, said energy storage circuit further configured to control the shape of said pulses to induce ultrasonic waves into at least one of said rails.

23. A railroad vehicle comprising:

a platform having a first end and a second end;

a truck coupled to said platform for supporting said platform on a pair of rails; and a rail ultrasonic wave inducement system comprising at least one magnetic exciter, a energy storage circuit electrically coupled to said at least one magnetic exciter, and a power source electrically coupled to said energy storage circuit, said at least one magnetic exciter coupled to said vehicle such that said at least one magnetic exciter is movable in concert with said vehicle and maintains a position adjacent to a rail, said energy storage circuit configured to supply at least one of sequential current pulses to said at least one magnetic exciter and simultaneous current pulses to said at least one magnetic exciter according to a predetermined configuration, said energy storage circuit further configured to control the shape of said pulses to induce ultrasonic waves into at least one of said rails.

* * * * *

UNITED STATES PATENT AND TRADEMARK OFFICE
CERTIFICATE OF CORRECTION

PATENT NO. : 6,742,392 B2 Page 1 of 1
DATED : June 1, 2004
INVENTOR(S) : Gilmore et al.

It is certified that error appears in the above-identified patent and that said Letters Patent is hereby corrected as shown below:

Column 7,
Line 19, after "locomotive" delete "a".
Line 35, after "to the first side of the rail" insert -- , --.
Line 36, after "second" delete "opposing".

Column 8,
Line 2, after "generating" delete "a".

Signed and Sealed this

Sixth Day of June, 2006

JON W. DUDAS
*Director of the United States Patent and Trademark Office*